United States Patent [19]

Stiller et al.

[11] Patent Number: 5,628,985
[45] Date of Patent: May 13, 1997

[54] COMPOSITIONS

[75] Inventors: Sigrid Stiller, Dormagen; Gertrud Kawa, Monheim, both of Germany

[73] Assignee: Lingner & Fischer GmbH, Germany

[21] Appl. No.: 452,201

[22] Filed: May 26, 1995

[30]  Foreign Application Priority Data

| Feb. 24, 1994 | [GB] | United Kingdom | 9403581 |
| May 27, 1994 | [GB] | United Kingdom | 9410654 |
| Dec. 2, 1994 | [GB] | United Kingdom | 9424346 |

[51] Int. Cl.⁶ .................. A61K 7/16; A61K 7/18
[52] U.S. Cl. .................................. 424/49; 424/52
[58] Field of Search ........................... 424/79-88

[56]  References Cited

U.S. PATENT DOCUMENTS

| 3,506,757 | 4/1970 | Salzmann . | |
| 3,538,230 | 11/1970 | Pader et al. | 424/50 |
| 3,689,637 | 9/1972 | Pader | 424/52 |
| 3,885,028 | 5/1975 | Cella et al. | 424/52 |
| 3,935,307 | 1/1976 | Aimoto et al. | 424/56 |
| 3,963,832 | 6/1976 | Hashimoto et al. | 424/56 |
| 4,108,978 | 8/1978 | Mazzanobile et al. | 424/49 |
| 4,172,121 | 10/1979 | Calvin et al. | 424/52 |
| 4,444,746 | 4/1984 | Harvey et al. . | |
| 4,772,461 | 9/1988 | Parran et al. | 424/52 |
| 5,178,869 | 1/1993 | Ebine et al. | 424/401 |
| 5,275,803 | 1/1994 | Dawson | 424/52 |
| 5,310,543 | 5/1994 | Dawson | 424/49 |
| 5,328,682 | 7/1994 | Pullen et al. | 424/49 |
| 5,328,692 | 7/1994 | Dana | 424/401 |

FOREIGN PATENT DOCUMENTS

WO94/01080  1/1994  WIPO .

*Primary Examiner*—Shep K. Rose
*Attorney, Agent, or Firm*—Nora Stein-Fernandez; William T. King; Edward T. Lentz

[57]  ABSTRACT

A transparent liquid dentifrice which comprises a particulate silica abrasive material present in from 10 to 15% by weight of the composition, stably suspended in an aqueous liquid vehicle with the aid of a suspending agent; and a humectant system which consists essentially of sorbitol, present in from 50 to 55% by weight of the composition (measured as the 100% active), and polyethylene glycol with average molecular weight in the range 200 to 600, present in from 0.5 to 3% by weight of the composition.

16 Claims, No Drawings

COMPOSITIONS

This is a continuation of PCT application Ser. No. PCT/EP95/00557 filed Feb. 15, 1995 which claimed priority from GB 9403581.3 filed on Feb. 24, 1994, GB9410654.9 filed on May 27, 1994 and GB9424346.6 filed Dec. 2, 1994.

The present invention relates to a liquid dentifrice, in particular a liquid dentifrice of improved clarity.

The term "liquid dentifrice" covers compositions which are intermediate between conventional toothpastes and mouthwashes. In order to match the tooth cleansing properties of a conventional toothbrush, it is preferred to include in a liquid dentifrice an abrasive such as silica. The inclusion of an abrasive however requires formulations which have a long term storage stability capacity, so that the abrasive particles do not settle out.

Thus U.S. Pat. No. 3,506,757 (Salzman et al) discloses liquid dentifrices in which the suspending agent is a xanthan (polysaccharide) gum. Since then, the xanthan gum system has been modified. GB 2 240 473-A (Lion) discloses liquid dentifrices containing a combination of a xanthan gum and a polyacrylate, the formulations having viscosities in the region 2,000 to 18,000 mPa s. PCT/EP93/01701 (WO 94/01080, Henkel) discloses liquid dentifrices containing a xanthan gum in combination with a hydroxypropyl-substituted hydrocolloid, a cationic nitrogen containing surfactant, an ampholytic surfactant, an N-acyl sarcosinate, an N-acyl tauride or a poly(ethylene glycol)/poly(propylene glycol) copolymer. Such formulations have viscosities in the range 2,000 to 10,000 mPa s (at 25° C.). In most instances, the formulations comprise well-known toothpaste humectants such as glycerine, propylene glycol, polyethylene glycol and sorbitol, more usually combinations thereof. EP 0 543 442-A (Unilever), however, discloses compositions containing a polysaccharide gum but in which the liquid medium is free from polyols such as sorbitol.

Transparent (visually clear) liquid dentifrices containing abrasives may be formulated by closely matching the refractive index of the liquid vehicle with that of the abrasive. Thus, GB 2 110 083 A (Colgate) discloses transparent liquid dentifrices containing glycerine (25%) and sorbitol (70% aq, 44–46%) and a thickening silica. WO 94/01080 (Henkel) discloses, in example 3, a transparent liquid dentifrice containing glycerine (86%, 28%), sorbitol (70% aq, 22%), polyethylene glycol 400 (3%) and ethanol (5%).

Whilst the concept of a liquid dentifrice has been well known in the an for several years, as witnessed by the above patent publications, there has been little commercial activity. Recently, however, Henkel have launched a translucent liquid dentifrice in various European markets, using the name "Thera-Med Liquid 2 in 1" in the UK, whilst Lion have launched a similar product in Japan, under the name "Brush".

There however remains the need to provide improved formulations which have greater consumer appeal. We have now surprisingly found that liquid dentifrices with improved transparency may be obtained by using a humectant system consisting of sorbitol and polyethylene glycol, avoiding other conventional humectants such as glycerin, in combination with a precipitated silica abrasive.

The present invention therefore provides a transparent liquid dentifrice which comprises a particulate silica abrasive material present in from 10 to 15% by weight of the composition, stably suspended in an aqueous liquid vehicle with the aid of a suspending agent; and a humectant system which consists essentially of sorbitol, present in from 50 to 55% by weight of the composition (measured as the 100% active), and polyethylene glycol with average molecular weight in the range 200 to 600, present in from 0.5 to 3% by weight of the composition.

Formulations according to the present invention have improved clarity and, therefore, enhanced consumer appeal, without the need to closely match the refractive indices of the silica abrasive and the liquid vehicle.

Suitable abrasive silicas for use in the present invention include synthetic amorphous silicas such as, precipitated silicas and silica gels. Preferred silicas have an average particle size between 1 and 20 µm, more preferably 1 and 15 µm and a surface area in the region 50 to 100 m$^2$/g, preferably 70 to 90 m$^2$/g (as measured by the BET method, DIN 66131). Suitable silica gels include silica xerogels such as those described in U.S. Pat. No. 3,538,230. Preferably the silica abrasive is a precipitated silica. Examples of suitable precipitated silicas include the product Sident 12 DS (Rhone-Poulenc).

Suitable suspending agents include natural gums such as xanthan gums; tragacanth; alkali metal alginates such as sodium alginate; and synthetic thickening agents such as carboxymethyl cellulose salts, such as sodium carboxymethyl cellulose or hydroxypropylmethyl cellulose and hydroxyethyl cellulose; and polyacrylic acid salts, for instance sodium polyacrylate. Preferably, the suspending agent is a xanthan gum or a carboxymethyl cellulose salt, particularly sodium carboxymethyl cellulose if a carboxymethyl cellulose salt is used A suitable sodium carboxymethyl cellulose is available commercially under the trade name Blanose CMC gum 12 M 8 PD, from Hercules Inc. Suitable such xanthan gums are described in U.S. Pat. No. 3,067,038 (O'Connell) and are available commercially under the trade name Keltrol from Kelco, Calif. U.S.A. Thickening silicas (pyrogenic silicas) should be avoided as they compromise the transparency of the formulation. Suitably, the suspending agent is present in an amount of between 0.01 and 3%, preferably between 0.01 and 2%, more preferably 0.01 to 1.0% by weight of the composition.

Suitably, sorbitol is used as a 70% aqueous solution. Preferably, this comprises from about 71 to about 79% by weight of the composition.

Suitable polyethylene glycols (PEG) include PEG 200 (PEG 4), PEG 300 (PEG 6), PEG 400 (PEG 8) and PEG 600 (PEG 12). Preferred PEGs have average molecular weights in the range 200 to 400.

Suitable surfactants for inclusion in the liquid vehicle include conventional anionic, nonionic and amphoteric surfactants or combinations thereof. Suitable anionic surfactants include alkali metal ($C_{12–18}$)alkyl sulphates, for instance sodium lauryl sulphate and N-acyl sarcosinates and N-acyl taurines in which the acyl moiety has from 12 to 16 carbon atoms, for instance, N-lauroyl, N-myristoyl and N-palmitoyl sarcosine alkali metal salts. Suitable nonionic surfactants include ($C_{8–16}$)- and (C 12–16)-fatty alcohol polyglycosides, for instance decyl polyglycose or lauryl polyglycose, available under the trade names Plantaren 2000 and Plantaren 1200 by Henkel. Other suitable nonionic surfactants include polycondensates of ethylene oxide and propylene oxide (poloxamers) and polyethoxylated sorbitol monoesters such as the products marketed under the name Tween by ICI. Suitable amphoteric surfactants include (long chain alkyl) amido (short chain alkyl) betaines such as coamidopropyl betaine. Suitably the surfactant system consists of an anionic surfactant or a combination of an annionic primary surfactant and a nonionic or amphoteric secondary or booster surfactant. Suitable such combinations include an alkali metal (C $_{12–18}$)alkyl sulphate and a (long chain alkyl)

amido (short chain alkyl) betaine or a fatty alcohol polyglycoside, preferably sodium lauryl sulphate and cocamidopropyl betaine, decyl polyglycose or lauryl polyglycose. Such surfactants are present in between 0.5 and 5%, preferably 1 and 3% by weight of the composition.

Liquid dentifrices of the present invention may also usefully comprise an anti-caries agent, for instance a fluoride ion source such as sodium fluoride and/or sodium monofluorophosphate, to provide between 250 and 2000 ppm, preferably 500 and 1500 ppm fluoride. There may also be included, when the anti-caries agent is sodium monofluorophosphate, other agents known to enhance the anti-caries activity of sodium monofluorophosphate, such as calcium glycerophosphate, which may be incorporated in a weight ratio of upto 1:3, preferably from 1:20 to 1:3, compared to the total weight of monofluorophosphate salt.

Liquid dentifrices of the present invention may also usefully comprise other oral hygiene agents, for instance:

- an antisensitivity agent such as a water soluble potassium salt, for instance potassium nitrate;
- an anti-calculus agent such as a water soluble alkali metal (dihydrogen)pyrophosphate salt, for instance tetrasodium pyrophosphate, an alkali metal tripolyphosphate salt such as sodium tripolyphosphate, or a phosphonate salt such as sodium azacycloheptane-2,2-diphosphonate; or
- an antiplaque agent such as a cationic antimicrobial agent, for instance chlorhexidine, or a water soluble salt thereof such as chlorhexidine diglucomte, or cetyl pyridinium chloride, a noncationic antimicrobial agent such as triclosan, or a bacteriocin such as nisin (available in a purified form as the product Ambicin N from Applied Microbiology Inc.).

Such agents, if present, will be included in a therapeutically effectively amount. The skilled man will appreciate that the co-formulation of a cationic antimicrobial agent such as chlorhexidine with an anionic surfactant such as sodium lauryl sulphate should be avoided.

The liquid vehicle will also comprise water, preferably deionised water, present in from 15 to 40, preferably 20 to 35% by weight of the composition (including the contribution from 70% aqueous solution of sorbitol, if used in this form).

The liquid vehicle may also contain other ingredients such as a flavouring agent, sweetening agent, breath freshening agent and colouring agent.

Liquid dentifrices according to the present invention may also comprise mica particles, to provide an element of glitter. This will enhance the visual appeal of the product, especially for children. Such mica particles will preferably be present in from 0.01 to 0.1%, preferably about 0.05% by weight of the composition.

Liquid dentifrices will have an orally acceptable pH, preferably between 5.5 and 8.0.

Liquid dentifrices of the present invention may be prepared using conventional processes, mixing together the ingredients in the appropriate quantities in any order that is convenient and thereafter, and if necessary, adjusting the final pH to desired value.

Liquid dentifrices according to the present invention will suitably have viscosities in the region 2,000 to 25,000 mPa s, preferably 5,000 to 20,000 mPa s (measured after 1 minute at 20° C. using a Brookfield apparatus with an RV5 spindle rotating at 10 rpm). Preferred viscosities give products which can be squeezed out of the dispenser as continuous strand onto a toothbrush and which do not then sink too far into the bristles.

Liquid dentifrices according to the present invention are characterised by their transparency. This can be measured on a HACH Ratio XR Turbidimeter. Values obtained using this instrument in the range 30 to 40 indicate a clear product. In comparison, translucent liquid dentifrices such as the Henkel product "Thera-Med Liquid 2 in 1" have a turbidity value in the range 750 to 850.

Liquid dentifrices according to the present invention are of use in oral hygiene, providing both cosmetic and therapeutic benefits. Suitably, the consumer will dispense about 1 g of the liquid dentifrice onto his toothbrush, to be then used in the same manner as a conventional toothpaste.

The present invention will now be illustrated by the following examples:

EXAMPLE 1

|  | % |
| --- | --- |
| sorbitol (70% aq) | 74.800 |
| silica (Sident 12 DS) | 12.000 |
| polyethylene glycol 200 | 2.000 |
| sodium lauryl sulphate | 1.700 |
| cocamidopropyl betaine | 1.000 |
| flavour | 0.800 |
| sodium saccharin | 0.250 |
| sodium monofluorophosphate | 0.750 |
| calcium glycerophosphate | 0.130 |
| xanthan gum | 0.100 |
| colouring (FD&C Blue no 1) | 0.003 |
| deionised water | qs |

Further dentifrice formulations were prepared having xanthan gum at 0.05, 0.15 and 0.20%, instead of 0.105 as above.

The various dentifrice formulations of Example 1 were found to have the following viscosities (measured at 20° C. using a Brookfield apparatus with an RV5 spindle rotating at 10 rpm):

| xanthan gum % | after 30 seconds (mPa s) | after 60 60 seconds (mPa s) |
| --- | --- | --- |
| 0.05 | 9,000 | 7,000 |
| 0.10 | 14,000 | 11,000 |
| 0.15 | 16,000 | 14,000 |
| 0.20 | 23,000 | 19,000 |

EXAMPLE 2

|  | % |
| --- | --- |
| sorbitol (70% aq) | 74.800 |
| silica (Sident 12 DS) | 12.000 |
| polyethylene glycol 200 | 2.000 |
| sodium lauryl sulphate | 1.700 |
| decyl polyglycose (Plantaren 2000) | 0.800 |
| flavour | 0.800 |
| sodium saccharin | 0.250 |
| sodium monofluorophosphate | 0.750 |
| calcium glycerophosphate | 0.130 |
| xanthan gum | 0.100 |
| colouring (FD&C Blue no 1) | 0.003 |
| deionised water | qs |

EXAMPLE 3

| | % |
|---|---|
| sorbitol (70% aq) | 74.500 |
| silica (Sident 12 DS) | 12.000 |
| polyethylene glycol 300 | 2.000 |
| sodium lauryl sulphate | 1.700 |
| decyl polyglycose (Plantaren 2000) | 1.000 |
| flavour | 0.800 |
| sodium monofluorophosphate | 0.750 |
| calcium glycerophosphate | 0.130 |
| xanthan gum | 0.100 |
| colouring (FD&C Blue no 1) | 0.003 |
| sodium saccharin | 0.250 |
| deionised water | qs |

EXAMPLE 4

| | % |
|---|---|
| sorbitol (70% aq) | 74.500 |
| silica (Sident 12 DS) | 12.000 |
| polyethylene glycol 300 | 2.000 |
| sodium lauryl sulphate | 1.700 |
| flavour | 0.800 |
| sodium saccharin | 0.250 |
| sodium monofluorophosphate | 0.750 |
| calcium glycerophosphate | 0.130 |
| xanthan gum | 0.100 |
| colouring (FD&C Blue no 1) | 0.003 |
| deionised water | qs |

EXAMPLE 5

| | % |
|---|---|
| sorbitol (70% aq) | 74.21 |
| silica (Sident 12 DS) | 12.00 |
| polyethylene glycol 300 | 2.00 |
| sodium lauryl sulphate | 1.70 |
| lauryl polyglucose (Plantaren 1200) | 1.00 |
| flavour | 0.80 |
| sodium saccharin | 0.25 |
| sodium monofluorophosphate | 0.91 |
| calcium glycerophosphate | 0.13 |
| sodium carboxymethylcellulose | 0.20 |
| colouring (Brilliant Blue 1%) | 0.30 |
| deionised water | qs |
| Viscosity | 9480 mPa s |
| pH-value | 6.1 |

EXAMPLE 6

| | % |
|---|---|
| sorbitol (70% aq) | 74.11 |
| silica (Sident 12 DS) | 12.00 |
| polyethylene glycol 300 | 2.00 |
| sodium lauryl sulphate | 1.70 |
| lauryl polyglucose (Plantaren 1200) | 1.00 |
| flavour | 0.80 |
| sodium saccharin | 0.25 |
| sodium monofluorophosphate | 0.91 |
| calcium glycerophosphate | 0.13 |
| sodium carboxymethylcellulose | 0.30 |
| colouring (Brilliant Blue 1%) | 0.30 |

-continued

| | % |
|---|---|
| deionised water | qs |
| | 11240 mPa s |
| pH-value | 6.07 |

EXAMPLE 7

| | % |
|---|---|
| sorbitol (70% aq) | 78.100 |
| silica (Sident 12 DS) | 12.000 |
| polyethylene glycol 300 | 3.000 |
| sodium lauryl sulphate | 1.700 |
| lauryl polyglucose (Plantaren 1200) | 1.000 |
| flavour | 0.800 |
| sodium saccharin | 0.250 |
| sodium monofluorophosphate | 0.760 |
| calcium glycerophosphate | 0.130 |
| sodium carboxymethylcellulose | 0.500 |
| colouring (Brilliant Blue 1%) | 0.003 |
| deionised water | qs |

EXAMPLE 8

| | % |
|---|---|
| sorbitol (70% aq) | 76.200 |
| silica (Sident 12 DS) | 12.000 |
| polyethyleneglycol 300 | 4.000 |
| sodium lauryl sulphate | 1.700 |
| cocamidopropylbetaine | 1.000 |
| flavour | 0.800 |
| sodium fluoride | 0.275 |
| colour | 0.003 |
| sodium carboxycellulose | 0.250 |
| water | qs |

Two of the carboxymethylcellulose (CMC) dentifrice formulations were found to have the following viscosities (measured at 20° C. using a Brookfield apparatus with an RV5 spindle rotating at 10 rpm):

| 0.20% CMC | 9840 mPa s |
|---|---|
| 0.30% CMC | 13840 mPa s |

We claim:

1. A transparent liquid dentifrice which consists essentially of water as an aqueous liquid vehicle in from 15 to 40% by weight of the composition, a particulate silica abrasive material having an average particle size between 1 and 20 µm present in from 10 to 15% by weight of the composition, stably suspended in the liquid vehicle with the aid of a suspending agent; and a humectant system which consists essentially of sorbitol, present in from 50 to 55% by weight of the composition (measured as the 100% active), and polyethylene glycol with average molecular weight in the range 200 to 600, present in from 0.5 to 3% by weight of the composition, wherein the overall viscosity of the dentifrice is sufficient to enable the dentifrice to be squeezed out of a dispenser as a continuous strand and not to sink into a toothbrush containing such strand, said dentifrice being free of thickening silicas or pyrogenic silicas.

2. A liquid dentifrice as claimed in claim 1 in which the particulate silica abrasive material is a precipitated silica.

3. A liquid dentifrice as claimed in claim 1 in which the suspending agent is a natural gum, tragacanth, an alkali metal alginate or a synthetic thickening agent.

4. A liquid dentifrice as claimed in claim 1 in which the natural gum is a xanthan gum.

5. A liquid dentifrice as claimed in claim 1 in which the synthetic thickening agent is a carboxymethyl cellulose salt.

6. A liquid dentifrice as claimed in claim 1 in which the carboxymethyl cellulose salt is sodium carboxymethyl cellulose.

7. A liquid dentifrice as claimed in claims 1 in which the suspending agent is present in an amount of between 0.01 and 3 by weight of the composition.

8. A liquid dentifrice as claimed in claim 1 which further comprises a surfactant system which is an anionic surfactant, a nonionic surfactant, an amphoteric surfactant or a combination thereof.

9. A liquid dentifrice as claimed in claim 8 in which the surfactant system is an anionic surfactant or a combination of an anionic primary surfactant and a nonionic or amphoteric secondary surfactant.

10. A liquid dentifrice as claimed in claim 8 in which the nonionic surfactant is a $(C_{8-16})$- or $(C_{12-16})$-fatty alcohol polyglycoside.

11. A liquid dentifrice as claimed in claim 8 in which the amphoteric surfactant is a (long chain alkyl) amido (short chain alkyl) betaine.

12. A liquid dentifrice as claimed in claim 8 in which the anionic surfactant is an alkali metal $(C_{12-18})$alkyl sulphate.

13. A liquid dentifrice as claimed in claim 1 which further comprises a fluoride ion source.

14. A liquid dentifrice as claimed in claim 1 which further comprises an anti-sensitivity agent, an anti-calculus agent or an anti-plaque agent or a combination thereof.

15. A method of preparing a liquid dentifrice as claimed in claim 1 of the preceding claims which comprising mixing together the ingredients in the appropriate quantities and thereafter adjusting the final pH to an orally acceptable value.

16. A method of preparing a liquid dentifrice as claimed in claim 8 of the preceding claims which comprising mixing together the ingredients in the appropriate quantities and thereafter adjusting the final pH to an orally acceptable value.

* * * * *